(12) United States Patent
Silver

(10) Patent No.: US 9,532,969 B2
(45) Date of Patent: *Jan. 3, 2017

(54) METHOD FOR TREATING PSORIASIS

(75) Inventor: Michael E. Silver, Holland, MI (US)

(73) Assignee: The William M. Yarbrough Foundation, Peoria, IL (US)

( * ) Notice: Subject to any disclaimer, the term of this patent is extended or adjusted under 35 U.S.C. 154(b) by 502 days.

This patent is subject to a terminal disclaimer.

(21) Appl. No.: 13/351,616

(22) Filed: Jan. 17, 2012

(65) Prior Publication Data

US 2012/0202878 A1 Aug. 9, 2012

Related U.S. Application Data

(60) Provisional application No. 61/440,608, filed on Feb. 8, 2011, provisional application No. 61/502,090, filed on Jun. 28, 2011.

(51) Int. Cl.
*A61K 31/26* (2006.01)
*A61P 17/06* (2006.01)
*A61K 47/48* (2006.01)

(52) U.S. Cl.
CPC ......... *A61K 31/26* (2013.01); *A61K 47/48038* (2013.01)

(58) Field of Classification Search
CPC .................. A61K 31/26; A61K 47/48038
USPC .................................................. 514/514
See application file for complete search history.

(56) References Cited

U.S. PATENT DOCUMENTS

2011/0195103 A1* 8/2011 Perez Arcas et al. ........ 424/401

OTHER PUBLICATIONS

Saint-Mezard et al., Eur. J. Dermatol. 2004, 14, 284-295.*
Weber et al., The Journal of Emergency Medicine, 1999, 17 (2), 235-237.*
Robert et al., New Engl. J. Med. 1999,341 (24), 1817-1828.*
Wikipedia—Isothiocyanate page.*

* cited by examiner

*Primary Examiner* — Sarah Pihonak
*Assistant Examiner* — Jason A Deck
(74) *Attorney, Agent, or Firm* — King & Partners, PLC

(57) ABSTRACT

A method for treating psoriasis including the steps of applying an isothiocyanate functional surfactant to an area affected by psoriasis, wherein the isothiocyanate functional surfactant comprises at least one isothiocyanate functional group associated with an aliphatic and/or aromatic carbon atom of the isothiocyanate functional surfactant.

1 Claim, No Drawings

METHOD FOR TREATING PSORIASIS

CROSS-REFERENCE TO RELATED APPLICATIONS

This application claims the benefit of U.S. Provisional Application Ser. No. 61/440,608, entitled "METHOD FOR TREATING PSORIASIS," filed Feb. 8, 2011 and U.S. Provisional Application Ser. No. 61/502,090, entitled "METHOD FOR TREATING PSORIASIS," filed Jun. 28, 2011—all of which are hereby incorporated herein by reference in their entirety, including all references cited therein.

BACKGROUND OF THE INVENTION

1. Field of the Invention

The present invention relates in general to a method for treating psoriasis and, more particularly, to a method for treating a plurality of forms of psoriasis including, but not limited to, plaque psoriasis, guttate psoriasis, inverse psoriasis, pustular psoriasis, erythrodermic psoriasis, scalp psoriasis, and nail psoriasis—just to name a few.

2. Background Art

According to the National Institutes of Health, psoriasis is a chronic, autoimmune disease, which affects approximately 7 to 10 million Americans, and approximately 80 to 120 million individuals worldwide.

Psoriasis typically manifests physical symptoms on the skin of an individual, and is believed to occur when the individual's immune system sends out faulty and/or inaccurate signals that speed up the growth cycle of skin cells. Psoriasis is not believed to be contagious.

Psoriasis is generally, but not always, characterized by patches of thick, red, inflamed skin and dry, silvery flakes of skin known as scales. Symptoms range in severity from barely noticeable to severe outbreaks of lesions that cover most of the body.

Forms of Psoriasis. There are seven general forms of psoriasis, namely: plaque, guttate, inverse, pustular, erythrodermic, scalp, and nail.

(I) Plaque psoriasis (i.e., psoriasis vulgaris) is the most prevalent form of the disease. About 80 percent of those who have psoriasis have this type. Plaque psoriasis is normally characterized by raised, inflamed, red lesions covered by a silvery white scale. It is typically found on the elbows, knees, scalp and/or the lower back of an individual.

(II) Guttate psoriasis is a form of psoriasis that often starts in childhood or young adulthood. The word guttate is derived from the Latin word meaning "drop." This form of psoriasis appears as small, red, individual spots on the skin. Guttate lesions usually appear on the trunk and limbs. These spots are not usually as thick as plaque lesions. Guttate psoriasis, often times, comes on quite suddenly. A variety of conditions can bring on an attack of guttate psoriasis, including upper respiratory infections, streptococcal throat infections (i.e., strep throat), tonsillitis, stress, injury to the skin and/or the administration of certain drugs including, but not limited to, antimalarials and beta-blockers.

(III) Inverse psoriasis is typically found in the armpits, groin, under the breasts, and in other skin folds around the genitals and the buttocks. This type of psoriasis appears as bright-red lesions that are smooth and shiny. Inverse psoriasis is subject to irritation from rubbing and sweating because of its location in skin folds and tender areas. Inverse psoriasis can be more troublesome in overweight people and those with deep skin folds.

(IV) Pustular psoriasis, which is often seen in adults, is characterized by white blisters of noninfectious pus (comprising of white blood cells) surrounded by red skin. Pustular psoriasis may be localized to certain areas of the body, such as the hands and feet, or covering most of the body. It typically begins with the reddening of the skin followed by formation of pustules and scaling.

Pustular psoriasis may be triggered by internal medications, irritating topical agents, overexposure to electromagnetic radiation (e.g., ultraviolet (UV) radiation), pregnancy, systemic steroids, infections, stress and/or sudden withdrawal of systemic medications and/or potent topical steroids.

(V) Erythrodermic psoriasis is a particularly inflammatory form of psoriasis that affects most of the body surface. It may occur in association with pustular psoriasis, and is characterized by periodic, widespread, fiery redness of the skin and the shedding of scales in sheets, rather than smaller flakes. The reddening and shedding of the skin are often accompanied by severe itching and pain, heart rate increase, and fluctuating body temperature. Erythrodermic psoriasis can be very serious and can causes protein and/or fluid loss that can lead to severe and prolonged illness. Erythrodermic psoriasis may also bring on infection, pneumonia, and congestive heart failure. People with severe cases of this condition often require hospitalization.

Known triggers of erythrodermic psoriasis include the abrupt withdrawal of a systemic psoriasis treatment including cortisone, allergic reaction to a drug resulting in the Koebner response, severe sunburns, infection, and medications such as lithium, anti-malarial drugs; and strong coal tar products.

(VI) Scalp psoriasis appears as red, itchy areas with silvery white scales on the scalp. One may notice flakes of dead skin in hair or on the shoulders, especially after scratching the scalp.

(VII) Nail psoriasis can affect both fingernails and toenails, causing pitting, abnormal nail growth and discoloration. Psoriatic nails may become loose and separate from the nail bed (i.e., onycholysis). Severe cases of nail psoriasis may cause the nail to crumble.

While no one knows exactly what causes psoriasis, it is believed that the immune system and/or genetics play substantial roles in its development. Most researchers agree that the immune system is somehow mistakenly triggered and/or excited, which causes a series of events, including acceleration of skin cell growth. A normal skin cell matures and falls off the body in approximately 28 to 30 days. A skin cell in a patient with psoriasis takes only 3 to 4 days to mature and instead of falling off (shedding), the cells pile up on the surface of the skin, forming psoriatic lesions.

Scientists believe that at least 10 percent of the general population inherits one or more of the genes that create a predisposition to psoriasis. However, only about 2-5 percent of the population develops the disease. Researchers believe that for a person to develop psoriasis, the individual likely has a combination of the genes that cause psoriasis and is exposed to specific external factors known as "triggers."

Psoriasis triggers are not believed to be universal. As such, what may cause one individual's psoriasis to become active, may not affect another. However, generally established psoriasis triggers include: stress, injury to the skin (e.g., Koebner phenomenon), and medications (e.g., lithium, antimalarials, plaquenil, quinacrine, chloroquine, hydroxychloroquine, beta-blockers, inderal, quinidine, indomethacin, etcetera).

Although scientifically unproven, some people with psoriasis suspect that alcohol consumption, allergies, diet, infections, smoking, stress, and weather trigger their psoriasis.

To the best of Applicant's knowledge, there is no known cure for psoriasis. Treatments for psoriasis are typically divided into three main types, namely: topical treatments, light therapy and/or oral medications.

Topical treatments include, for example, corticosteroids, vitamin D analogues, anthralin, retinoids, calcineurin inhibitors, salicylic acid, coal tar, and moisturizers.

Light therapy or treatments include, for example, sunlight, UVB phototherapy, narrowband UVB therapy, photochemotherapy, or psoralen plus ultraviolet A (PUVA), and excimer laser.

Oral medications include, for example, retinoids, methotrexate, cyclosporine, hydroxyurea, immunomodulator drugs (biologics).

While the above-identified medical treatments do appear to provide at least some relief to those who are afflicted by psoriasis, such treatment remains non-desirous and/or problematic inasmuch as, among other things, none of the above-identified treatments provide sufficient therapeutic relief from the debilitating effects of psoriasis without material drawbacks.

It is therefore an object of the present invention to provide a method for treating psoriasis which offers timely relief from the symptoms presented when one is afflicted with psoriasis.

These and other objects of the present invention will become apparent in light of the present specification, claims, and drawings.

SUMMARY OF THE INVENTION

In one embodiment, the present invention is directed to a method for treating psoriasis comprising the step of: applying an isothiocyanate functional surfactant to an area affected by psoriasis, wherein the isothiocyanate functional surfactant comprises at least one isothiocyanate functional group associated with an aliphatic and/or aromatic carbon atom of the isothiocyanate functional surfactant.

In another embodiment of the present invention, the method for treating psoriasis further comprises the step of removing the isothiocyanate functional surfactant from the area affected by psoriasis.

In yet another exemplary embodiment, the present invention is directed to a method for treating psoriasis comprising the steps of: (a) applying an isothiocyanate functional surfactant to an area affected by psoriasis, wherein the isothiocyanate functional surfactant comprises at least one isothiocyanate functional group associated with an aliphatic and/or aromatic carbon atom of the isothiocyanate functional surfactant; (b) removing the isothiocyanate functional surfactant from the area affected by psoriasis; and (c) repeating the steps of applying and removing the isothiocyanate functional surfactant to/from the affected area.

The present invention is also directed to a method for treating psoriasis comprising the step of: washing an area affected by psoriasis with an isothiocyanate functional surfactant, wherein the isothiocyanate functional surfactant comprises at least one isothiocyanate functional group associated with an aliphatic and/or aromatic carbon atom of the isothiocyanate functional surfactant.

The present invention is further directed to a method for treating psoriasis comprising the step of: applying a lysine derivative to an area affected by psoriasis, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

The present invention is still further directed to a method for treating psoriasis comprising the step of: applying a surfactant to an area affected by psoriasis, wherein the protonated form of the surfactant is represented by the following chemical structure:

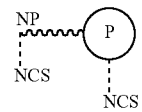

wherein the surfactant comprises a non-polar moiety (NP) and a polar moiety (P), and wherein at least one isothiocyanate functional group (NCS) is associated with the polar and/or non-polar moiety.

In another embodiment, the present invention is directed to a method for treating psoriasis, comprising the step of: applying a surfactant or a pharmaceutically acceptable salt thereof to an area affected by psoriasis, wherein the protonated form of the surfactant is represented by the following chemical structure:

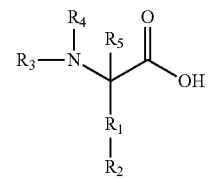

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

The present invention is also directed to a method for treating psoriasis comprising the step of: applying a surfactant or a pharmaceutically acceptable salt thereof to an area affected by psoriasis, wherein the protonated form of the surfactant is represented by the following chemical structure:

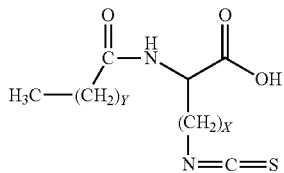

wherein X comprises an integer ranging from approximately 1 to approximately 25, and wherein Y comprises an integer ranging from approximately 6 to approximately 25.

In a preferred embodiment, the present invention is directed to a method for treating psoriasis comprising the step of: applying a surfactant or a pharmaceutically acceptable salt thereof to an area affected by psoriasis, wherein the protonated form of the surfactant is represented by the following chemical structure:

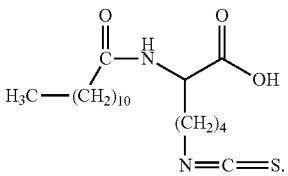

In another embodiment, the present invention is directed to a method for treating psoriasis, comprising the step of: applying a surfactant or a pharmaceutically acceptable salt thereof to an area affected by psoriasis, wherein the deprotonated form of the surfactant is represented by the following chemical structure:

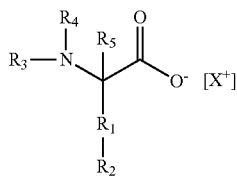

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4^+$, wherein Z comprises, H, $R_6$, and/or $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In yet another preferred embodiment, the present invention is directed to a method for treating psoriasis as disclosed supra, further comprising the step of applying an additional surfactant, wherein the additional surfactant is selected from at least one of the group comprising a non-ionic surfactant, an anionic surfactant, a cationic surfactant, a zwitterionic surfactant, and combinations thereof.

DETAILED DESCRIPTION OF THE INVENTION

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

In accordance with the present invention, surprisingly effective methods for treating psoriasis are provided herein. In particular, methods for treating a plurality of types of psoriasis including plaque psoriasis, guttate psoriasis, inverse psoriasis, pustular psoriasis, erythrodermic psoriasis, scalp psoriasis, and nail psoriasis are disclosed.

In one embodiment, the present invention is directed to a method for treating psoriasis comprising the steps of applying one or more isothiocyanate functional surfactants to an area affected by psoriasis. Preferably, the isothiocyanate functional surfactant comprises one or more isothiocyanate functional groups associated with an aliphatic and/or aromatic carbon atom of the isothiocyanate functional surfactant. It will be understood that an area affected by psoriasis may comprise areas proximate and/or contiguous to areas where a manifestation of physical symptoms are present. Physical symptoms include, for example, discomfort, itching, burning, erythema, blistering, scaling, epidermal necrosis, desquamation, discoloration, and/or hyperpigmentation—just to name a few. It will be further understood that isothiocyanate functional surfactants, regardless of their ordinary meaning, are defined herein as a surfactant having an isothiocyanate functional group associated therewith. It will be yet further understood that the term associated as used herein in chemical context, regardless of its ordinary meaning, is defined herein as attached, a covalent bond, a polar covalent bond, an ionic bond, a hydrogen bond, van der Waals forces, electrostatic interaction, directly and/or indirectly linked, etcetera.

The term surfactant derives from contraction of the terms surface-active-agent and is defined herein as a molecule and/or group of molecules which are able to modify the interfacial properties of the liquids (aqueous and non-aqueous) in which they are present. The surfactant properties of these molecules reside in their amphiphilic character which stems from the fact that each surfactant molecule has both a hydrophilic moiety and a hydrophobic (or lipophilic) moiety, and that the extent of each of these moieties is balanced so that at concentrations at or below the critical micelle concentration (i.e., CMC) they generally concentrate at the air-liquid interface and materially decrease the interfacial tension. For example, sodium salts of saturated carboxylic acids are extremely soluble in water up to C8 length and are thus not true surfactants. They become less soluble in water from C9 up to C18 length, the domain of effective surfactants for this class of compounds. The carboxylic acids (fatty acids) can be either saturated or unsaturated starting from C16 chain lengths.

Without being bound by any one particular theory, it is believed that the isothiocyanate functional surfactants disclosed herein facilitate treatment of numerous forms of psoriasis by boosting the body's immune system. It is also believed that the isothiocyanate functional surfactants disclosed herein facilitate elevating phase II enzymes (e.g., HAD(P)H quinine oxidoreductase) which are believed to, among other things regulate inflammatory responses within the body, as well as detoxify carcinogens and/or activated carcinogens.

In accordance with the present invention, the isothiocyanate functional surfactants may be used as a topical leave-on product in which one or more surfactants remain on the skin and are not immediately and/or ever rinsed off away from the skin. Alternatively, the isothiocyanate functional surfactants of the present invention may be used as a topical wash in an apply-and-rinse fashion. For either case, it is preferred that the isothiocyanate functional surfactants be generally mild to human skin (e.g., non-irritating or low-irritating). In particular, anionic N-alkanoyl surfactants derived from amino acids are especially preferred because, while not completely predictable, they have a tendency to be mild. The methods of preparation detailed in this invention employ, but are not limited to, amino acids that possess at least two amine functionalities, at least one of which is converted to an N-alkanoyl functionality, and at least one of which is converted into isothiocyanate functionality. The amino acids include, but are not limited to, the α-amino acids lysine, ornithine, 2,4-diaminobutanoic acid, 2,3-diaminoproprionic acid, 2,7-diaminoheptanoic acid, and 2,8-diaminooctanoic acid. Additionally, amino acids other than α-amino acids may be employed, such as β-amino acids, etcetera. It will be understood that amino acid derived surfactants are preferred due to their mild nature, but any one of a number of other surfactants are likewise contemplated for use in accordance with the present invention.

Methods for preparing isothiocyanate functional surfactants and/or their precursors can involve, but are not limited to, conversion of an amine functionality to an isothiocyanate functionality. The methods of conversion of amine functionalities to isothiocyanate functionalities include, but are not limited to: (1) reaction with carbon disulfide to yield an intermediate dithiocarbamate, followed by reaction with ethylchloroformate or its functional equivalent such as bis (trichloromethyl)-carbonate, trichloromethyl chloroformate, or phosgene; (2) reaction with thiophosgene; (3) reaction with 1,1'-thiocarbonyldiimidizole; (4) reaction with phenyl-thiochloroformate; (5) reaction with ammonium or alkali metal thiocyanate to prepare an intermediate thiourea followed by cleaving to the isothiocyanate via heating; and (6) reaction with an isothiocyanato acyl halide [SCN—$(CH_2)_n$—CO—Cl]. The resulting isothiocyanate functional surfactant, depending on the method of preparation, can be isolated as a pure material or as a mixture with other surfactants. The resulting isothiocyanate functional surfactant, depending on the method of preparation, can be isolated and used directly in nonionic form, anionic form, cationic form, zwitterionic (amphoteric) form, and/or in a neutral surfactant-precursor form in combination with a base such as sodium hydroxide or triethanol amine if the neutral surfactant-precursor form possesses a protonated carboxylic acid group such that reaction (deprotonation) with the base converts the neutral surfactant-precursor form to an anionic surfactant, or in neutral surfactant-precursor form in combination with an acid if the neutral surfactant-precursor form possess amine functionality such that reaction (protonation) with the acid converts the neutral surfactant-precursor form to a cationic surfactant.

In accordance with the present invention the step of applying comprises, but is not limited to, spraying, dripping, dabbing, rubbing, blotting, dipping, and any combination thereof.

In a preferred embodiment of the present invention, the isothiocyanate functional surfactant is removed from the affected area after a period of time. Such a period comprises, but is not limited to, seconds (e.g., 1 second, 2 seconds, 5 seconds, 10 seconds, 15 seconds, 20 seconds, 30 seconds, 45 seconds, and 60 seconds), minutes (e.g., 1 minute, 2 minutes, 5 minutes, 10 minutes, 15 minutes, 20 minutes, 30 minutes, 45 minutes, and 60 minutes), hours (e.g., 1 hour, 2 hours, 4 hours, 5 hours, 8 hours, 10 hours, 15 hours, 24 hours, 36 hours, 48 hours, and 60 hours), days (e.g., 1 day, 2 days, 3 days, 4 days, 5 days, 6 days, 7 days, 10 days, 14 days, 21 days, 30 days), etcetera. It will be understood that the step of removing preferably occurs via rinsing, wiping, and/or extracting—just to name a few.

Depending upon the subject and/or the severity of the psoriasis, multiple applications may be necessary. As such, the steps of applying and/or removing the isothiocyanate functional surfactant may be repeated one or a plurality of times.

The present invention is also directed to a method for treating psoriasis comprising the step of applying a lysine derivative to an area affected by psoriasis, wherein the lysine derivative comprises an α-nitrogen and a ε-nitrogen. Preferably, an alkyl substituent comprising at least approximately 8 carbon atoms is associated with the α-nitrogen. Preferably, at least one isothiocyanate functional group is associated with the ε-nitrogen.

The present invention is further directed to a method for treating psoriasis comprising the step of: applying a surfactant to an area affected by psoriasis, wherein the surfactant is represented by the following chemical structure:

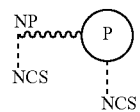

and wherein the surfactant comprises a non-polar moiety (NP) and a polar moiety (P), and wherein at least one isothiocyanate functional group (NCS) is associated with the polar and/or non-polar moiety.

The present invention is yet further directed to a method for treating psoriasis, comprising the step of: applying a surfactant or a pharmaceutically acceptable salt thereof to an area affected by psoriasis, wherein the protonated form of the surfactant is represented by the following chemical structure:

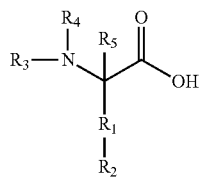

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

In this embodiment, the surfactant is preferably represented by the following chemical structure:

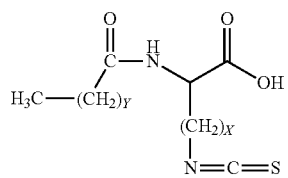

wherein X comprises an integer ranging from approximately 1 to approximately 25, and wherein Y comprises an integer ranging from approximately 6 to approximately 25.

More preferably, the surfactant is represented by the following chemical structure:

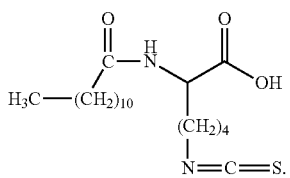

In another embodiment, the present invention is directed to a method for treating psoriasis comprising the step of: applying a surfactant or a pharmaceutically acceptable salt thereof to an area affected by psoriasis, wherein the deprotonated form of the surfactant is represented by the following chemical structure:

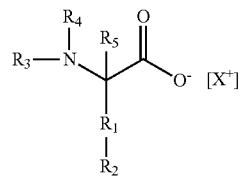

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4^+$, wherein Z comprises, H, $R_6$, and/or $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In accordance with the present invention, the isothiocyanate functional surfactant may also be associated with one or more additional surfactants, wherein the additional surfactants are selected from at least one of the group comprising a non-ionic surfactant, an anionic surfactant, a cationic surfactant, a zwitterionic surfactant, and combinations thereof.

Non-limiting examples of preferred anionic surfactants include taurates; isethionates; alkyl and alkyl ether sulfates; succinamates; alkyl sulfonates, alkylaryl sulfonates; olefin sulfonates; alkoxy alkane sulfonates; sodium and potassium salts of fatty acids derived from natural plant or animal sources or synthetically prepared; sodium, potassium, ammonium, and alkylated ammonium salts of alkylated and acylated amino acids and peptides; alkylated sulfoacetates; alkylated sulfosuccinates; acylglyceride sulfonates, alkoxyether sulfonates; phosphoric acid esters; phospholipids; and combinations thereof. Specific anionic surfactants contemplated for use include, but are by no means limited to, ammonium cocoyl isethionate, sodium cocoyl isethionate, sodium lauroyl isethionate, sodium stearoyl isethionate, sodium lauroyl sarcosinate, sodium cocoyl sarcosinate, sodium lauryl sarcosinate, disodium laureth sulfosuccinate, sodium lauryl sulfoacetate, sodium cocoyl glutamate, TEA-cocoyl glutamate, TEA cocoyl alaninate, sodium cocoyl taurate, potassium cetyl phosphate.

Non-limiting examples of preferred cationic surfactants include alkylated quaternary ammonium salts $R_4NX$; alkylated amino-amides $(RCONH—(CH_2)_n)NR_3X$; alkylimidazolines; alkoxylated amines; and combinations thereof. Specific examples of anionic surfactants contemplated for use include, but are by no means limited to, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, distearyl methyl ammonium chloride, distearyl methyl ammonium bromide, ditallow dimethyl ammonium chloride, ditallow dimethyl ammonium sulfate, di(hydrogenated tallow) dimethyl ammonium chloride, di(hydrogenated tallow)dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosulfate, stearimidopropyldimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, ditallowyl oxyethyl dimethyl ammonium chloride, behenamidopropyl PG dimonium chloride, dilauryl dimethyl ammonium chloride, distearly dimethyl ammonium chloride, dimyristyl dimethyl ammonium chloride, dipalmityl dimethyl ammonium chloride, distearyl dimethyl ammonium chloride, stearamidoproyl PG-dimonium chloride phosphate, stearamidopropyl ethyldiammonium ethosulfate, stearamidopropyl dimethyl(myristyl acetate)ammonium chloride, stearimidopropyl dimethyl cetaryl ammonium tosylate, stearamido propyl dimethyl ammonium chloride, stearamidopropyl dimethyl ammonium lactate.

Non-limiting examples of preferred non-ionic surfactants include alcohols, alkanolamides, amine oxides, esters (including glycerides, ethoxylated glycerides, polyglyceryl esters, sorbitan esters, carbohydrate esters, ethoxylated carboxylic acids, phosphoric acid triesters), ethers (including ethoxylated alcohols, alkyl glucosides, ethoxylated polypropylene oxide ethers, alkylated polyethylene oxides, alkylated polypropylene oxides, alkylated PEG/PPO copolymers), silicone copolyols. Specific examples of non-ionic surfactants contemplated for use include, but are by no means limited to, cetearyl alcohol, ceteareth-20, nonoxynol-9, C12-15 pareth-9, POE(4) lauryl ether, cocamide DEA, glycol distearate, glyceryl stearate, PEG-100 stearate, sorbitan stearate, PEG-8 laurate, polyglyceryl-10 trilaurate, lauryl glucoside, octylphenoxy-polyethoxyethanol, PEG-4 laurate, polyglyceryl diisostearate, polysorbate-60, PEG-200 isostearyl palmitate, sorbitan monooleate, polysorbate-80.

Non-limiting examples of preferred zwitterionic or amphoteric surfactants include betaines; sultaines; hydroxysultaines, amido betaines, amidosulfo betaines; and combinations thereof. Specific examples of amphoteric surfactants contemplated for use include, but are by no means limited to, cocoamidopropyl sultaine, cocoamidopropyl hydroxyl sultaine, cocoamidopropylbetaine, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl (2-bis-hydroxy) carboxymethyl betaine, stearyl bis-(2-hydroxyethyl) carboxymethyl betaine, oelyl dimethyl gamma-carboxypropyl betaine, lauryl bis-(2-hydroxypropyl)alpha carboxymethyl betaine, coco dimethyl sulfopropyl betaine, stearyl dimethyl sulfopropyl betaine, lauryl dimethyl sulfoethyl betaine, lauryl bis(2-hydroxyethyl) sulfopropyl betaine, oleyl betaine, cocamidopropyl betaine.

The invention is further described by the following examples.

Example I

Preparation of a Mixture of $N_\alpha$-lauroyl-$N_\epsilon$-isothiocyanato-L-Lysine with $N_\alpha,N_\epsilon$-bis-lauroyl-L-lysine A 1 liter beaker equipped with an overhead mechanical stainless steel paddle stirrer was charged with 100 mL of 1 M NaOH (0.100 mol). Stirring was initiated and the beaker cooled to −5° C. to −10° C. using a salt/ice bath. Next, 23.4 g (0.100 mol) of $N_\epsilon$-benzylidene-L-lysine (prepared via the method of Bezas, B. and Zervas, L., JACS, 83, 1961, 719-722) was added. Immediately afterward and while keeping the solution cold, 140 mL (0.140 mol) of precooled (in a salt/ice bath) 1 M NaOH and 26.1 mL of lauroyl chloride was added in two equal portions over a period of 6 minutes. The mixture was stirred for 10 more minutes at −5 to −10° C., then the ice bath was removed and the reaction mixture allowed to stir for another 1 hour while warming to room temperature. Next, the reaction mixture was cooled using a salt/ice bath and then sufficient concentrated HCl was added to adjust the pH to 7.5-7.8. With the pH at 7.8-7.8 and with continued cooling and stirring, 4.6 mL (60% of stoichiometric, 0.068 mol) of thiophosgene was added dropwise via an additional funnel over the period of 1 hour. During this time, sufficient 1 M NaOH was added to maintain a pH range between 7.5-7.8. After the thiophosgene addition was complete, additional 1 M NaOH was added as necessary until the pH stabilized in 7.5-7.8 range. Next, sufficient 30% NaOH was added to adjust the pH to approximately 8.5. Next, 12 mL (0.051 mol) of lauroyl chloride was rapidly added, followed by sufficient 1 M NaOH to keep the pH in the range of 8.00-8.50. Next, sufficient concentrated HCl was added to adjust the pH to 1.5. The reaction mixture was filtered via vacuum filtration, and the precipitate washed with dilute HCl (pH=2). The product, a white moist solid, was dried in vacuo while heating to 60° C. 45.19 g of white solid product was recovered, a mixture of predominantly $N_\alpha$-lauroyl-$N_\epsilon$-isothiocyanato-L-lysine and $N_\alpha,N_\epsilon$-bis-lauroyl-L-lysine (determined via LC-MS analysis). Both compounds in this mixture can be simultaneously converted into anionic (carboxylate) surfactants via reaction with aqueous NaOH to yield a clear aqueous solution of the surfactants.

Example II

Preparation of Pure $N_\alpha$-lauroyl-$N_\epsilon$-isothiocyanato-L-Lysine

Step 1: Preparation of $N_\alpha$-lauroyl-$N_\epsilon$-carbobenzoxy-L-Lysine 60.0 g of $N_\epsilon$-cbz-L-Lysine (cbz is carbobenzoxy) purchased from Atomole Scientific Company, LTD was added to a three-liter beaker along with 1200 mL of RO water and the mixture was stirred. Next, 39 mL of 30% aqueous NaOH was added, resulting in dissolution of the $N_\epsilon$-cbz-L-Lysine. The resulting solution was cooled in an ice bath and then 52.5 mL of lauroyl chloride was added. The ice bath was removed 30 minutes later, and stirring continued for an additional six hours, at which time 18 mL of concentrated hydrochloric acid was added. The reaction mixture was then filtered via vacuum filtration, the white solid product washed with 1 M aqueous HCl, and then the solid product was dried in vacuo while heated to approximately 85° C. 96.5 g of dry white solid product was obtained. The product is further purified by dissolving it in methanol, filtering off any insoluble precipitate, and removing the methanol in vacuo to recover a white solid product (mp 99.5-103.0° C.).

Step 2: Preparation of $N_\alpha$-lauroyl-$N_\epsilon$-ammonium chloride-L-Lysine 10.0 g of $N_\alpha$-lauroyl-$N_\epsilon$-carbobenzoxy-L-Lysine was weighed into a one liter Erlenmeyer flask equipped with a magnetic stir bar. 150 mL of concentrated hydrochloric acid was added and the solution was stirred and heated in an oil bath to 104° C., then allowed to cool with the oil bath back to room temperature. The solution was then cooled to 9° C. for approximately four hours, during which time a large mass of white precipitate formed. The reaction mixture was filtered in vacuo and rinsed with a small amount of cold 1 M HCl. The white solid reaction product was then dried in vacuo while being heated to 78° C., yielding 7.89 g of white solid product (mp 191-193° C.).

Step 3: Preparation of $N_\alpha$-lauroyl-$N_\epsilon$-isothiocyanato-L-Lysine 0.46 mL of thiophosgene was added to 30 mL of dichloromethane in a 125 mL Erlenmeyer flask equipped with a magnetic stir bar. To this solution was drop wise added over 15 minutes a solution consisting of 2.00 g $N_\alpha$-lauroyl-$N_\epsilon$-ammonium chloride-L-Lysine, 10 mL RO water, and 2.7 mL 20% aqueous NaOH. Stirring was continued for an additional 30 minutes, after which sufficient concentrated hydrochloric acid was added to lower the pH to 1 as indicated by testing with pHydrion paper. The reaction solution was then transferred into a separatory funnel and the bottom turbid dichloromethane layer was isolated and dried with anhydrous magnesium sulfate and gravity filtered. To the filtrate was added 50 mL of hexanes. The solution was then concentrated via removal of 34 mL of solvent via trap-to-trap distillation and then placed in a −19° C. freezer. A mass of white precipitate formed after a few hours and was isolated via vacuum filtration and then dried in vacuo for 2 hours. 1.130 g of a slightly off white solid powder product was obtained [mp 37.0-39.0° C.; IR (cm$^{-1}$), 3301sb, 2923s, 2852s, 2184m, 2099s, 1721s, 1650s, 1531s, 1456m, 1416w, 1347m, 1216m, 1136w]. Analysis (Midwest Microlab, LLC): Calculated: C, 61.58%; H, 9.25%; N, 7.56%; O, 12.95%; S, 8.65%. Actual: C, 61.64%; H, 9.21%; N, 7.58%; O, 13.01%; S, 8.55%.

Step 4: Isolation of Sodium $N_\alpha$-lauroyl-$N_\epsilon$-isothiocyanato-L-Lysinate Via Lyophilization 0.147 g of $N_\alpha$-lauroyl-$N_\epsilon$-isothiocyanato-L-Lysine was combined and stirred with 2 g of RO water and 0.39 mL of 1.00 M NaOH in a 50 mL single neck round bottom flask and filtered into a 250 mL single neck round bottom flask to yield a clear pale amber solution. The flask was then immersed while rotating into a dry ice/acetone bath to yield a solid coating on the walls of the flask, whereupon the flask was evacuated (0.10 mm Hg) and removed from the ice bath. Evacuation for one hour yielded a dry white solid powder of the water soluble surfactant Sodium $N_\alpha$-lauroyl-$N_\epsilon$-isothiocyanato-L-Lysinate. [mp 47-55° C. to small droplets of clear colorless viscous liquid; IR (mineral oil mull, cm$^{-1}$), 3300m amide N—H str; 2188s, 2107s N═C str; 1627s, amide C═O str; 1593s carboxylate C═O str]

Example III

Preparation of a Two-Part Formulation for the Treatment of Psoriasis

A two-part formulation for topical application to the skin was prepared as follows:

Part I: A 25% by mass mixture of $N_\alpha$-lauroyl-$N_\epsilon$-isothiocyanato-L-Lysine in Dow Corning DC344 fluid (a mixture of octamethyl-cyclotetrasiloxane and decamethyl-cyclopentasiloxane) was prepared in a mortar and pestle to produce a paste that was loaded into a 5 ml plastic disposable syringe. A syringe needle was not employed. Rather, the dispensing end of the syringe was capped except for when dispensing without a syringe needle into the palm of a hand occurred.

Part II: Part II consisted of Cetaphil Moisturizing Lotion to which additional triethanol amine (TEA) was added such that the concentration of the additional triethanol amine was 0.006 g triethanol amine per gram of lotion, raising the pH of the Cetaphil Lotion from 7.74 to 8.77.

Preferred Instructions for Application of Formulation to the Skin: A 0.2 mL portion of the $N_\alpha$-lauroyl-$N_\epsilon$-isothiocyanato-L-Lysine/DC344 mixture is dispensed from the syringe into the palm of a hand (approximately 0.13 g of the mixture). Next, two full squirts of the Cetaphil/TEA lotion is dispensed on top of the $N_\alpha$-lauroyl-$N_\epsilon$-isothiocyanato-L-Lysine/DC344 mixture (approximately 2.8 g of the lotion). Next, using the index finger of the other hand, the components are mixed thoroughly for approximately 30 seconds, during which time the water insoluble $N_\alpha$-lauroyl-$N_\epsilon$-isothiocyanato-L-Lysine surfactant-precursor is deprotonated to yield the water-soluble anionic (carboxylate) surfactant and yield a homogenous smooth white lotion (this reduces the pH to 7.4). This mixture is then applied to the afflicted areas by gently rubbing it on as one would apply any moisturizing lotion. Treatment is recommended two to three times per day until the symptoms of the psoriasis subside.

Example IV

Preparation of a One-Part Formulation for the Treatment of Psoriasis

A one-part formulation for topical application to the skin was prepared as follows:

First, 0.00025% (by wt.; 5.0 micromolar) of Sodium $N_\alpha$-lauroyl-$N_\epsilon$-isothiocyanate-L-Lysinate, the sodium salt of the material provided in step three of Example II, was mixed with 2% Lauryl PEG-10 Methyl Ether Dimethicone (commercially available from Clear Chemical Corporation, Holland, Mich.) which was QS to achieve 100% with 2,6,10,15,19,23-Hexamethyltetracosane (commercially available from Sigma-Aldrich). It will be understood that the concentration of Sodium $N_\alpha$-lauroyl-$N_\epsilon$-isothiocyanate-L-Lysinate may range from approximately 0.000001% to approximately 50%. Non-limiting examples of additional concentrations include 0.0005%, 0.005%, 0.005%, 0.005%, 0.05%, 0.5%, 5% —just to name a few. It will be further understood that the concentration of Lauryl PEG-10 Methyl Ether Dimethicone may range from approximately 0.000001% to approximately 50%.

Preferred Instructions for Application of the One-Part Formulation to the Skin: A 0.1-1.0 mL portion of the one-part formulation is dispensed from a container into the palm of a hand for subsequent administration to an affected area and/or is dispensed directly onto an affected area by gently rubbing it on as one would apply a moisturizing lotion. Treatment is recommended one to four times per day until the symptoms of the psoriasis subside.

Example V

Preparation of a One-Part Formulation for the Treatment of Psoriasis

A one-part oil-based formulation for topical application to the skin was prepared as follows:

Lyophilized Sodium $N_\alpha$-lauroyl-$N_\epsilon$-isothiocyanato-L-Lysinate (0.15 g) is dissolved in 29.85 g of refined jojoba oil while stirring and warming to 50° C. to give a clear colorless solution that is 0.50% by mass Sodium $N_\alpha$-lauroyl-$N_\epsilon$-isothiocyanato-L-Lysinate. Next, 0.10 g of this solution was combined with 69.90 g of refined jojoba oil, 20.0 g of heavy mineral oil, and 10.0 g of squalane to yield an oil-based formulation that is 0.00050% by mass Sodium $N_\alpha$-lauroyl-$N_\epsilon$-isothiocyanato-L-Lysinate. The oils employed are provided for the purposes of illustration, and are not to be construed as limiting the invention in any way. As such, the oils may be liquid, solid, or gel, and may be synthetic or of natural origin and include but are not limited to waxes, esters, lipids, fats, glycerides, cyclic silicones, linear silicones, crosslinked silicones, alkylsilicones, silicone copolyols, alkylated silicone copolyols, and/or hydrocarbons, and/or ethoxylated versions of all of these.

The foregoing description merely explains and illustrates the invention and the invention is not limited thereto except insofar as the appended claims are so limited, as those skilled in the art who have the disclosure before them will be able to make modifications without departing from the scope of the invention.

What is claimed and desired to be secured by Letters Patent of the United States is:

1. A method for treating plaque psoriasis, comprising the step(s) of:

applying a one-part oil-based formulation comprising jojoba oil, mineral oil, squalene, and a surfactant or a pharmaceutically acceptable salt thereof to an area affected by plaque psoriasis, wherein the protonated form of the surfactant is represented by the following chemical structure:

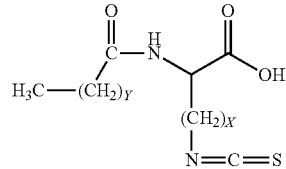

wherein X comprises an integer ranging from approximately 1 to approximately 25, and wherein Y comprises an integer ranging from approximately 6 to approximately 25.

* * * * *